United States Patent
Farr

Patent Number: 6,020,497
Date of Patent: Feb. 1, 2000

[54] 3-SUBSTITUTES ISOXAZOLIDINES AS CHIRAL AUXILIARY AGENTS

[75] Inventor: Roger N. Farr, Whitehouse Station, N.J.

[73] Assignee: Merck & Co., Inc., Rahway, N.J.

[21] Appl. No.: 09/169,658

[22] Filed: Oct. 9, 1998

Related U.S. Application Data

[60] Provisional application No. 60/062,114, Oct. 14, 1997.

[51] Int. Cl.$^7$ .................................................. C07D 261/02
[52] U.S. Cl. ............................................................ 548/240
[58] Field of Search ............................................. 548/240

[56] References Cited

U.S. PATENT DOCUMENTS 5,561,178  10/1996  Prabhu ...................... 524/95

OTHER PUBLICATIONS

A. Abiko et al., "New Isoxazolidine–based Chiral Auxiliaries for Asymmetric Syntheses," Tetrahedron Letters, Vol. 38, No. 18, pp. 3261–3264, (1997).

A. Abiko et al., "Benzopyranoisoxazolidines as Chiral Auxiliaries for Asymmetric Synthesis," Angew. Chem. Int. Ed. Engl., Vol. 34, No. 7, pp. 793–795 (1995).

Ca 115: 92853z Asymmetric syntheses of . . . cycloaddition. Keirs et al., p. 826, 1991.

*Primary Examiner*—Joseph K. McKane
*Attorney, Agent, or Firm*—Philippe L. Durette; Melvin Winokur; Carol S. Quagliato

[57] ABSTRACT

Disclosed are compounds of the formula:

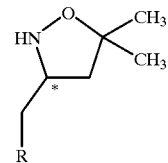

(I)

where R is selected from the group consisting of $C_1$–$C_4$ linear or branched alkyl, trifluoromethyl, halo, phenyl, biphenyl and naphthyl, wherein the aromatic group can be substituted with $C_1$–$C_4$ linear or branched alkyl, trifluoromethyl, or halo; and wherein the asterisked 3-position ring carbon is either in (R) or (S) configuration, or racemate form, and salts thereof formula I. The compounds are useful in chiral synthesis, for example, producing naturally occurring L-amino acids, e.g., alanine, from aliphatic acid precursors.

6 Claims, No Drawings

3-SUBSTITUTES ISOXAZOLIDINES AS CHIRAL AUXILIARY AGENTS

CROSS-REFERENCE TO RELATED APPLICATIONS

The present invention claims priority of U.S. provisional application Serial No. 60/062,114 filed Oct. 14, 1997, the contents of which are hereby incorporated by reference.

STATEMENT REGARDING FEDERALLY-SPONSORED R&D

Not applicable.

REFERENCE TO MICROFICHE APPENDIX

Not applicable.

FIELD OF THE INVENTION

This invention relates to the use of chiral auxiliaries in chiral synthesis of biologically important molecules.

BACKGROUND OF THE INVENTION

The use of chiral auxiliaries is a valuable tool in the synthesis of complex natural products. Usually natural products occur as optically active molecules, and conventional organic synthesis generally produces the racemic mixture, comprised of non-optically active forms, which require complex resolution into their optically active components. The use of chiral auxiliaries in a synthetic procedure have the big advantage of producing one or the other optically active form directly without resorting to complex resolution techniques.

Different classes of chiral auxiliaries are known in the art for the stereoselective synthesis of many natural products, including naturally occurring amino acids. See for example, Evan's oxazolidinones[1], Oppolzer's sultams[2], Meyer's oxazolines[3] and others[4], which have been developed for asymmetric synthesis of biological molecules. (See in back for reference cites.) Further, Masamune and coworkers have reported benzopyranoisoxazolidines[6] and bicyclicisoxazolidines as chiral auxiliaries[7].

What is constantly being searched for in the art is a new class of chiral auxiliaries which offer greater ease and versatility in their application for producing optically active natural products.

SUMMARY OF THE INVENTION

We have discovered that certain 3-substituted isoxazolidines are effective chiral auxiliary agents in stereoselectively directing the chirality in the synthesis of biologically important molecules. For example, the use of 3-substituted isoxazolidines are especially useful in the synthesis of naturally occurring products including amino acids, e.g. alanine, from readily available precursors, e.g. propionic acid. They are also useful in the multi-step synthesis of intermediates in the total synthesis of the immunoregulant, FK-506 (Fujisawa).

What is provided by this invention is a compound of the formula:

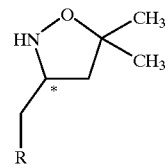

(I)

where R is selected from the group consisting of $C_1$–$C_4$ linear or branched alkyl, trifluoromethyl, halo, phenyl, biphenyl and naphthyl, wherein the aromatic group can be substituted with 1–3 of $C_1$–$C_4$ linear or branched alkyl, trifluoromethyl, or halo; and wherein the asterisked 3-position ring carbon is either in (R) or (S) configuration, or racemate form, and salts thereof formula I.

Further provided is a compound of the formula:

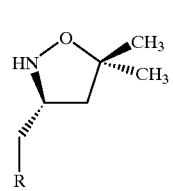

(Ia)

where R is selected from the group consisting of $C_1$–$C_4$ linear or branched alkyl, trifluoromethyl, halo, phenyl, biphenyl and naphthyl, wherein the aromatic group can be substituted with 1–3 of $C_1$–$C_4$ linear or branched alkyl, trifluoromethyl, or halo; and salts thereof formula Ia.

Furthermore there is provided a compound of the formula:

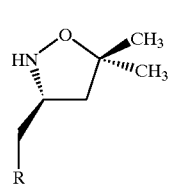

(Ib)

where R is selected from the group consisting of $C_1$–$C_4$ linear or branched alkyl, trifluoromethyl, halo, phenyl, biphenyl and naphthyl, wherein the aromatic group can be substituted with 1–3 of $C_1$–$C_4$ linear or branched alkyl, trifluoromethyl, or halo; and salts thereof formula Ib.

In addition there is provided a compound of Structure I, Ia, Ib, wherein R is selected from t-butyl, phenyl, 4-biphenyl and 2-naphthyl.

There is also provided a compound wherein the ring nitrogen is acylated with $R_1$—CO—, where $R_1$ is $C_1$–$C_4$ linear or branched alkyl and having the structure II:

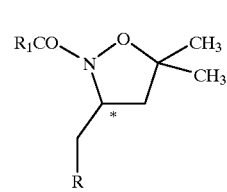

(II)

and where R is selected from the group consisting of $C_1$–$C_4$ linear or branched alkyl, trifluoromethyl, halo, phenyl, biphenyl and naphthyl, wherein the aromatic group can be substituted with 1–3 of $C_1$–$C_4$ linear or branched alkyl, trifluoromethyl, or halo; and wherein the asterisked 3-position ring carbon is either in (R) or (S) configuration, or racemate form, and salts thereof formula II.

There is also provided a compound wherein the ring nitrogen is acylated with $R_1$—CO—, where $R_1$ is $C_1$–$C_4$ linear or branched alkyl and having the structure IIa:

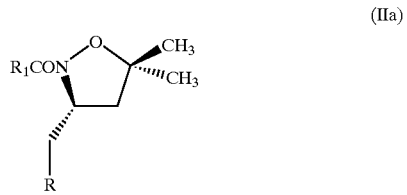

(IIa)

and where R is selected from the group consisting of $C_1$–$C_4$ linear or branched alkyl, trifluoromethyl, halo, phenyl, biphenyl and naphthyl, wherein the aromatic group can be substituted with 1–3 of $C_1$–$C_4$ linear or branched alkyl, trifluoromethyl, or halo; and salts thereof formula IIa.

There is also provided a compound wherein the ring nitrogen is acylated with $R_1$—CO—, where $R_1$ is $C_1$–$C_4$ linear or branched alkyl and having the structure IIb:

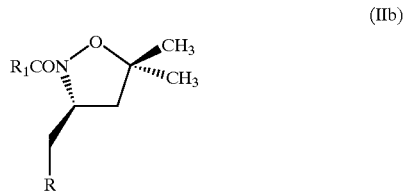

(IIb)

and where R is selected from the group consisting of $C_1$–$C_4$ linear or branched alkyl, trifluoromethyl, halo, phenyl, biphenyl and naphthyl, wherein the aromatic group can be substituted with 1–3 of $C_1$–$C_4$ linear or branched alkyl, trifluoromethyl, or halo; and salts thereof formula IIb.

In addition there is provided a compound of Structure II, IIa, IIb, wherein R is selected from t-butyl, phenyl, 4-biphenyl and 2-naphthyl.

DETAILED DESCRIPTION OF THE INVENTION

As used herein, the term "$C_1$–$C_4$ linear or branched alkyl" includes n-, iso-, sec- and t-butyl, n- or isopropyl, ethyl and methyl; the term "halo" includes fluoro, chloro, bromo and iodo; the term "biphenyl" includes 2-, 3-, and 4-biphenyl; the term "naphthyl" includes 1- and 2-naphthyl.

The aromatic group of phenyl, biphenyl and naphthyl can be substituted with 1–3 substituents selected from $C_1$–$C_4$ linear or branched alkyl, trifluoromethyl and halo, as defined above.

Representative examples of substituted aromatics include 4-tolyl, 2-ethylphenyl, 3-t-butylphenyl, 2,4-dichlorophenyl, 4-trifluoromethylphenyl, 4'-chloro-4-biphenyl, 2'-methyl-4-biphenyl, 4-bromo-2-naphthyl, and the like.

Synthesis of the subject 3-substituted isoxazolidines is readily achievable as is seen by the following Scheme 1. They are readily acylated, and are crystalline solids rendering ease in use in chiral synthesis and are readily available. The synthesis of chiral (>98% enantiomeric excess) 3-substituted isoxazolidines can be carried out starting with either the (R) or (S) optically active form of glycidyl tosylate to establish the desired reagent stereochemistry.

The useful chiral auxiliaries are the compounds of Structure I in the (R) or (S) configurations. However, the racemate is also useful since it can be made in a non-chiral synthesis, which may perhaps be more convenient, and then resolved into its respective (R) and (S) stereoisomers via conventional resolution techniques.

As seen in Scheme 1, glycidyl tosylate VI, (either enantiomer) is incorporated into a "double-Grignard" reaction sequence to obtain the isoxazolidines IV. In the first step, a hydrocarbon (represented by R) bromide V is converted to the magnesium bromide salt and allowed to react with glycidyl tosylate to afford the hydroxy tosylate VII. Next is the stepwise treatment with potassium ethoxide and isopropenyl magnesium bromide to produce the homoallylic alcohol VIII, which can be isolated via crystallization. Mesylation of VIII followed by nucleophilic displacement by hydroxyl amine results in the hydroxylamine IX, which can be then treated with triflic acid in methylene chloride to afford the desired isoxazolidine IV. (Note: the wavy line in the structures is attached to the 3-position ring carbon which can be either the (R) or (S) form, or the racemate mixture thereof.). Note that the initial asterisked asymmetric carbon in the glycidate VI is converted to the opposite configuration in the final isoxazolidine 4, where it becomes the 3-position ring carbon in the isoxazolidine ring.

Acylation under Schotten-Baumann conditions is essentially instantaneous and quantitative for a variety of acid chlorides, containing $R^1$, including acetyl, propionyl, isobutanoyl chloride, and the like.

The specific synthesis of 4, wherein R is 4-biphenyl, is seen in Scheme 2. Glycidyl tosylate[11] 6 (the (S) enantiomer) was reacted with 4-(phenyl)-phenyl magnesium bromide to afford the hydroxy tosylate 7. Following the stepwise treatment with potassium ethoxide and isopropenyl magnesium bromide, the resulting homo-allylic alcohol 8 is

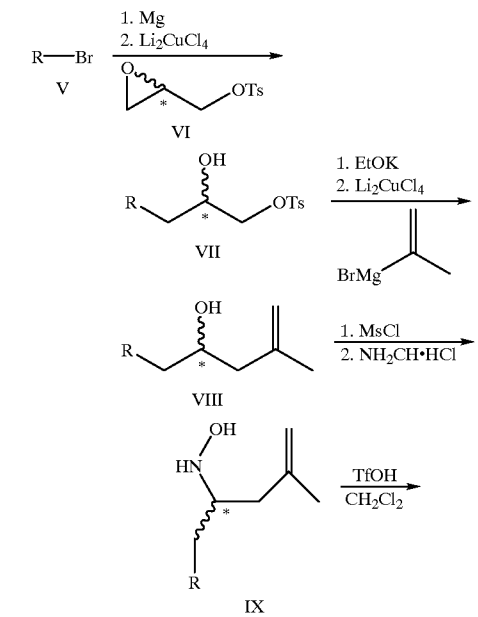

Scheme 1

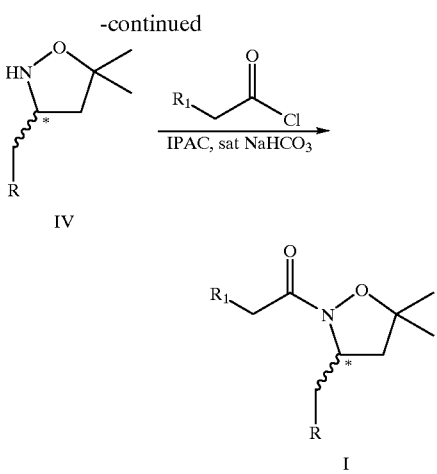

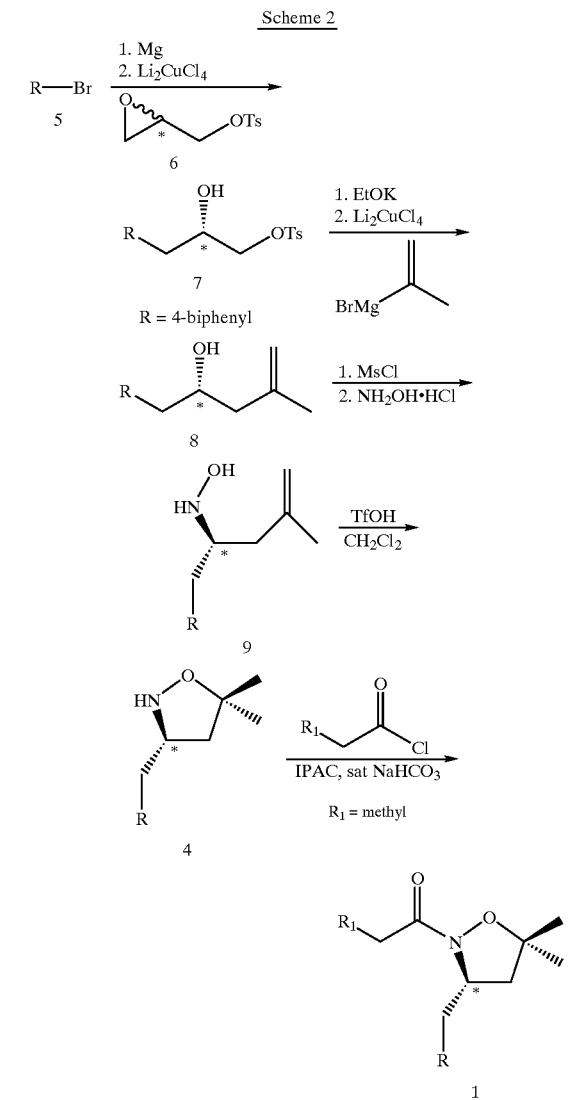

isolated via crystallization (96% assay, 85% isolated). Mesylation followed by nucleophilic displacement by hydroxyl amine results in the isolation of the hydroxylamine 9 in 53% yield, which is then treated with triflic acid in methylene chloride to afford the desired isoxazolidine 4 in 78% yield.

Note that the initial asterisked asymmetric carbon in the glycidate 6, the (S) stereoisomer, is converted to the opposite configuration in the final isoxazolidine 4, where it becomes the (R) stereoisomer in the 3-position of the isoxazolidine ring system.

Isoxazolidine 4 (the (R) stereisomer, where R is 4-biphenyl) is a crystalline solid (m.p. 104°–105° C.) with $\lambda_{max}$ at 254 nm. Detection with a standard UV lamp provides ready identification. Amide 1 (R=4-biphenyl, $R_1$=Me) is useful in a variety of specific asymmetric transformations including e.g., electrophilic amination to produce L-amino acids and synthesis of the immunoregulant FK-506, (see T. Jones et al., JACS, 1989, 111, pp. 1157–1159).

The following Examples are illustrative of carrying out the invention and should not be construed as being limitations on the scope or spirit of the instant invention

EXAMPLE 1

Synthesis of 7

Lithium tetrachlorocuprate (II) (0.05 eq, 375 mls of 0.1 M) was added to THF (200 mls) and the mixture cooled to −30° C. 4-biphenylmagnesium bromide (0.56 m in THF) was added via cannula over 5 minutes and the mixture was stirred for thirty minutes. This brown solution of the organocuprate was then added via cannula to a solution of (S) glycidyl tosylate (122 g, 0.53 m) in THF (500 mls) at −30° C. The mixture was stirred at this temperature for 1 hour and then quenched by adding aqueous ammonium chloride (500 mls). The aqueous layer was removed and the organic layer containing 7 was washed with water (2×100 mls) and then dried with magnesium sulfate and used as is in the next step.

EXAMPLE 2

Synthesis of 8

Compound 7 in the THF layer from Example 1 was treated with 1.2 equivalents of potassium ethoxide in THF (600 mls) at 0° C. The mixture was stirred for 1 hour and hycrochloric was added to quench the reaction. MTBE (300 mLs) was added ands the organic layer was washed with water (1×100 mL) and brine (1×100 mL). The organic layer was used as is in the next step.

Lithium tetrachlorocuprate (II) (0.10 eq, 466 mls of 0.1 M) was added to the above prepared THF layer (200 mls) and the mixture cooled to −30° C. Isopropenylmagnesium bromide (0.70 m, 1.4 L of 0.5 M in THF) was added via cannula over 5 minutes and the mixture was stirred for thirty minutes. This brown solution of the organocuprate was then added via cannula to the THF solution (500 mls) at −20° C. The mixture was stirred at this temperature for 1 hour and then quenched by adding aqueous ammonium chloride (500 mls). The aqueous layer was removed and the organic layer was washed with water (2×100 mls) and then dried with magnesium sulfate. The THF is removed and the product 8 dissolved in MTBE (200 mL) and filtered through a plug of silica gel and crystallized from heptane. Isolated yield for compound 8 in the three step process is 85%. The enantiomeric excess was determined by conventional means for the intermediate homo-allylic alcohol 8 prior to hydroxylamine inversion. The Mosher esters of the chiral and racemic materials were prepared and evaluated by NMR. The "wrong" enantiomer could not be detected. Therefore the assigned "ee" for 8 was greater than 98%.

EXAMPLE 3

Synthesis of 9

Compound 8 (15 g in 150 mL of THF) is treated with triethylamine (1.5 eq) and methanesulfonyl cloride at )° C. After 30 minutes, the mesylate was solvent switched to ethanol. Hydroxylamine hydrochloride (5 eq) and triethylamine (8 eq) were added and the mixture refluxed for 18 hrs. Ethanol was removed and MTBE (200 mL) was added. The organic layer was washed with water (100 mL) and brine (100 mL). Following silica gel chromatography, the product 9 is isolated in 53% yield.

EXAMPLE 4

Synthesis of 4

Compound 9 (12.3 grams in 150 mL of DCM) is treated with trifluoromethanesulfonic acid (1.1 eq in 50 mL of DCM) at −60° C. The dark mixture was allowed to warm to −20° C. and quenched with aqueous sodium bicarbonate. The DCM was removed and MTBE was added (200 mls). Following silica gel chromatography, the product 4 is isolated in 67% yield, as the (R) isomer.

EXAMPLE 5

Synthesis of 1

Compound 4 (540 mg in IPAC 5 mL) was treated with aqueous sodium bicarbonate and propionyl chloride (1.2 eq). The mixture was stirred for 30 minutes and the aqueous layer was removed. Following silica gel chromatography, the product 1, the 3(R)-isoxazolidine was isolated in 99% yield.

Note: To obtain the corresponding 3(S)-isoxazolidine isomer of 4, the starting glycidyl tosylate 6 used in the synthesis in Scheme 2 is the (R) isomer.

EXAMPLE 6

Synthesis of Alanine

Amide 1 (formed by reacting isoxazolidine 4 with propionic acid chloride as described above) is cooled to −78° C. in THF. Lithium hexamethyldisilazide is added followed by lithium tetrachlorocuprate (II). The reaction mixture is allowed to warm to 0° C. over 30 minutes and then recooled to −78° C. Lithium t-butyl-N-tosyloxycarbamate is then added over 5 minutes. The mixture is allowed to stir for several hours and then quenched with ammonium chloride and chromatographed to yield the naturally occurring L-alanine.

This protocol can be applied to any L-amino acid desired by appropriately changing the side chain on amide 1. For example, if $R_1$ is phenyl, then L-phenylalanine is produced. If $R_1$ is 2-propyl, then leucine is produced.

To obtain the corresponding D-amino acids, the corresponding 3(S) isoxazolidine isomer of 4 is utilized.

LIST OF REFERENCE CITES

1. Evans, D. A.; Ennis, M. D.; Mathre, D. J. *J. Am. Chem. Soc.* 1982, 104, 1737.
2. Oppolzer, W.; Moretti, R.; Thomi, S. *Tetrahedron Lett.* 1989, 30, 5603.
3. Lutomski, K. A.; Meyers, A. I. *Asymmetric Synthesis;* Morrison, J. D., Ed.; Academic Press: New York, 1984; 3, 1.
4. For Example: Drewes, S. E.; Malissar, D. G. S.; Roos, G. H. O. *Chem. Ber.* 1993, 126, 2663.
5. Nahm, S.; Weinreb, S. M. *Tetrahedron Lett.* 1981, 22, 3815.
6. Abiko, A.; Moriya, O.; Filla, S. A.; Masamune, S. *Angew. Chem. Int. Ed. Engl.* 1995, 34, 793.
7. Abiko, A.; Liu, J. F.; Wang, G.; Masamune, S. *Tetrahedron Lett..* 1997, 38, 3261.
8. Grunanger, P.; Vita-Finzi, P. *The Chemistry of Heterocyclic Chemistry;* Taylor, E. C. Ed.; Wiley-Interscience, New York, 1991, 49, 649.
9. Starting materials were prepared from the corresponding aldehydes via condensation with nitromethane/ borohydride reduction or oxime formation/chlorination Reported yields are from the aldehyde tions with Noyori or Burke catalysts were either slow or led to N—O bond scission. "OAB" based catalysts led to 40–60% ee (40–62% yield). See: Didier, E.; Loubinoux, B.; Ramos Tombo, G. M.; Rihs, G. *Tetrahedron* 1991, 47, 4941.
11. Klunder, J. M.; Onami, T.; Sharpless, K. B. *J. Org. Chem.* 1989, 54, 1295.

What is claimed:

1. A compound having the structure (II):

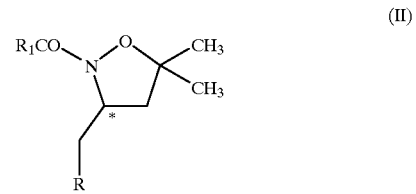

(II)

wherein the ring nitrogen is acylated with $R_1$—CO—, where $R_1$ is $C_1$–$C_4$ linear or branched alkyl, where R is selected from the group consisting of $C_1$–$C_4$ linear or branched alkyl, trifluoromethyl, halo, phenyl, biphenyl and naphthyl, wherein the aromatic group is optionally substituted with 1–3 of $C_1$–$C_4$ linear or branched alkyl, trifluoromethyl, or halo; and wherein the asterisked 3-position ring carbon is either in (R) or (S) configuration, or racemate form, and salts thereof formula II.

2. The compound of claim 1 wherein the ring nitrogen is acylated with $R_1$—CO—, where $R_1$ is $C_1$–$C_4$ linear or branched alkyl and having the structure IIa:

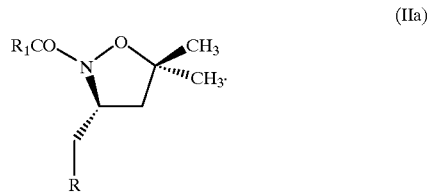

(IIa)

3. The compound of claim 1 wherein the ring nitrogen is acylated with $R_1$—CO—, where $R_1$ is $C_1$–$C_4$ linear or branched alkyl and having the structure IIb:

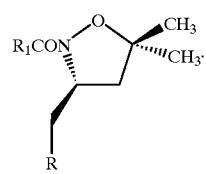
(IIb)
4. The compound of claim 1 wherein R is selected from t-butyl, phenyl, biphenyl and 2-naphthyl.
5. The compound of claim 2 wherein R is selected from t-butyl, phenyl, biphenyl and 2-naphthyl.
6. The compound of claim 3 wherein R is selected from t-butyl, phenyl, biphenyl and 2-naphthyl.
* * * * *